(12) United States Patent
Abunassar et al.

(10) Patent No.: US 10,426,473 B2
(45) Date of Patent: Oct. 1, 2019

(54) SYSTEM AND METHOD FOR PLICATING A HEART VALVE

(71) Applicant: Abbott Cardiovascular Systems Inc., Santa Clara, CA (US)

(72) Inventors: Chad Abunassar, San Francisco, CA (US); Koji J. Kizuka, San Francisco, CA (US); Casey M. Barbarino, San Francisco, CA (US); Brandon W. Chu, San Francisco, CA (US); Travis R. Marsot, Mountain View, CA (US); Shengmin Mei, Fremont, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 205 days.

(21) Appl. No.: 15/788,636

(22) Filed: Oct. 19, 2017

(65) Prior Publication Data

US 2019/0117223 A1    Apr. 25, 2019

(51) Int. Cl.

| A61B 17/08 | (2006.01) |
|---|---|
| A61F 2/24 | (2006.01) |
| A61B 17/122 | (2006.01) |
| A61B 17/00 | (2006.01) |
| A61B 17/128 | (2006.01) |

(52) U.S. Cl.
CPC .......... *A61B 17/083* (2013.01); *A61B 17/122* (2013.01); *A61F 2/24* (2013.01); *A61B 17/1285* (2013.01); *A61B 2017/00243* (2013.01); *A61B 2017/00292* (2013.01); *A61B 2017/00477* (2013.01); *A61B 2017/00526* (2013.01); *A61F 2/246* (2013.01); *A61F 2/2442* (2013.01)

(58) Field of Classification Search
CPC . A61B 17/083; A61B 17/122; A61B 17/1227; A61F 2/24; A61F 2/2442; A61F 2/2445; A61F 2/2454; A61F 2/246; Y10T 24/3431
See application file for complete search history.

(56) References Cited

U.S. PATENT DOCUMENTS

| 3,586,002 | A | * | 6/1971 | Wood | ................ | A61B 17/083 |
|---|---|---|---|---|---|---|
| | | | | | | 606/221 |
| 5,474,557 | A | * | 12/1995 | Mai | .................... | A61B 17/0642 |
| | | | | | | 606/219 |
| 6,015,417 | A | * | 1/2000 | Reynolds, Jr. | ....... | A61B 17/064 |
| | | | | | | 606/151 |

(Continued)

*Primary Examiner* — Ryan J. Severson
(74) *Attorney, Agent, or Firm* — David J. Pitman; Fulwider Patton LLP

(57) ABSTRACT

A device for connecting together two opposing leaflets of a valve in a patient's heart, comprising: a first clip having a generally U-shape, comprising a first prong and a second prong, and a first bridge connecting the first prong to the second prong; a second clip having a generally U-shape, comprising a third prong and a fourth prong, and a second bridge connecting the third prong to the fourth prong; a third clip having a generally U-shape, comprising a fifth prong and a sixth prong, and a third bridge connecting the fifth prong to the sixth prong, wherein the third prong has a first elongate axis and the fifth prong has a second elongate axis and the third prong and the fifth prong are positioned to extend adjacent to and parallel with the first prong, and are configured to rotate about the first elongate axis and the fifth elongate axis respectively.

17 Claims, 10 Drawing Sheets

(56) References Cited

U.S. PATENT DOCUMENTS

| | | | |
|---|---|---|---|
| 6,517,555 B1* | 2/2003 | Caro | A61B 17/122 128/898 |
| 6,537,286 B2* | 3/2003 | Acampora | A61B 17/083 606/151 |
| 6,719,767 B1* | 4/2004 | Kimblad | A61B 17/064 606/151 |
| 6,896,684 B2* | 5/2005 | Monassevitch | A61B 17/064 606/142 |
| 6,986,775 B2* | 1/2006 | Morales | A61B 17/00234 128/898 |
| 8,361,110 B2* | 1/2013 | Chanduszko | A61B 17/0057 606/151 |
| 8,545,525 B2* | 10/2013 | Surti | A61B 17/1114 24/547 |
| 8,968,393 B2* | 3/2015 | Rothstein | A61B 17/064 623/2.11 |
| 9,636,107 B2* | 5/2017 | Morales | A61B 17/00234 |
| 9,730,752 B2* | 8/2017 | Keller | A61B 17/122 |
| 10,004,514 B2* | 6/2018 | Ladjali | A61B 17/00234 |
| 2002/0099395 A1* | 7/2002 | Acampora | A61B 17/083 606/157 |
| 2002/0177859 A1* | 11/2002 | Monassevitch | A61B 17/064 606/139 |
| 2003/0233142 A1* | 12/2003 | Morales | A61B 17/00234 623/2.37 |
| 2004/0176783 A1* | 9/2004 | Edoga | A61B 17/0643 606/139 |
| 2005/0107810 A1* | 5/2005 | Morales | A61B 17/00234 606/143 |
| 2005/0267525 A1* | 12/2005 | Chanduszko | A61B 17/0057 606/213 |
| 2006/0025787 A1* | 2/2006 | Morales | A61B 17/00234 606/151 |
| 2006/0100646 A1* | 5/2006 | Hart | A61B 17/083 606/151 |
| 2006/0212049 A1* | 9/2006 | Mohiuddin | A61B 17/083 606/151 |
| 2008/0234701 A1* | 9/2008 | Morales | A61B 17/00234 606/139 |
| 2008/0234702 A1* | 9/2008 | Morales | A61B 17/00234 606/139 |
| 2011/0054489 A1* | 3/2011 | Pan | A61B 17/122 606/120 |
| 2011/0106109 A1* | 5/2011 | Surti | A61B 17/1114 606/142 |
| 2012/0277853 A1* | 11/2012 | Rothstein | A61B 17/064 623/2.11 |
| 2013/0123808 A1* | 5/2013 | Chanduszko | A61B 17/00234 606/142 |
| 2013/0178880 A1* | 7/2013 | Keller | A61B 17/122 606/158 |
| 2015/0182216 A1* | 7/2015 | Morales | A61B 17/00234 623/2.36 |
| 2016/0038149 A1* | 2/2016 | Ladjali | A61B 17/00234 606/142 |
| 2016/0287383 A1* | 10/2016 | Rowe | A61F 2/2427 |
| 2017/0258591 A1* | 9/2017 | Ladjali | A61B 17/122 |
| 2017/0303929 A1* | 10/2017 | Keller | A61B 17/122 |
| 2017/0333042 A1* | 11/2017 | Sato | A61B 17/00234 |
| 2018/0325671 A1* | 11/2018 | Abunassar | A61F 2/2466 |
| 2019/0117223 A1* | 4/2019 | Abunassar | A61B 17/083 |

* cited by examiner

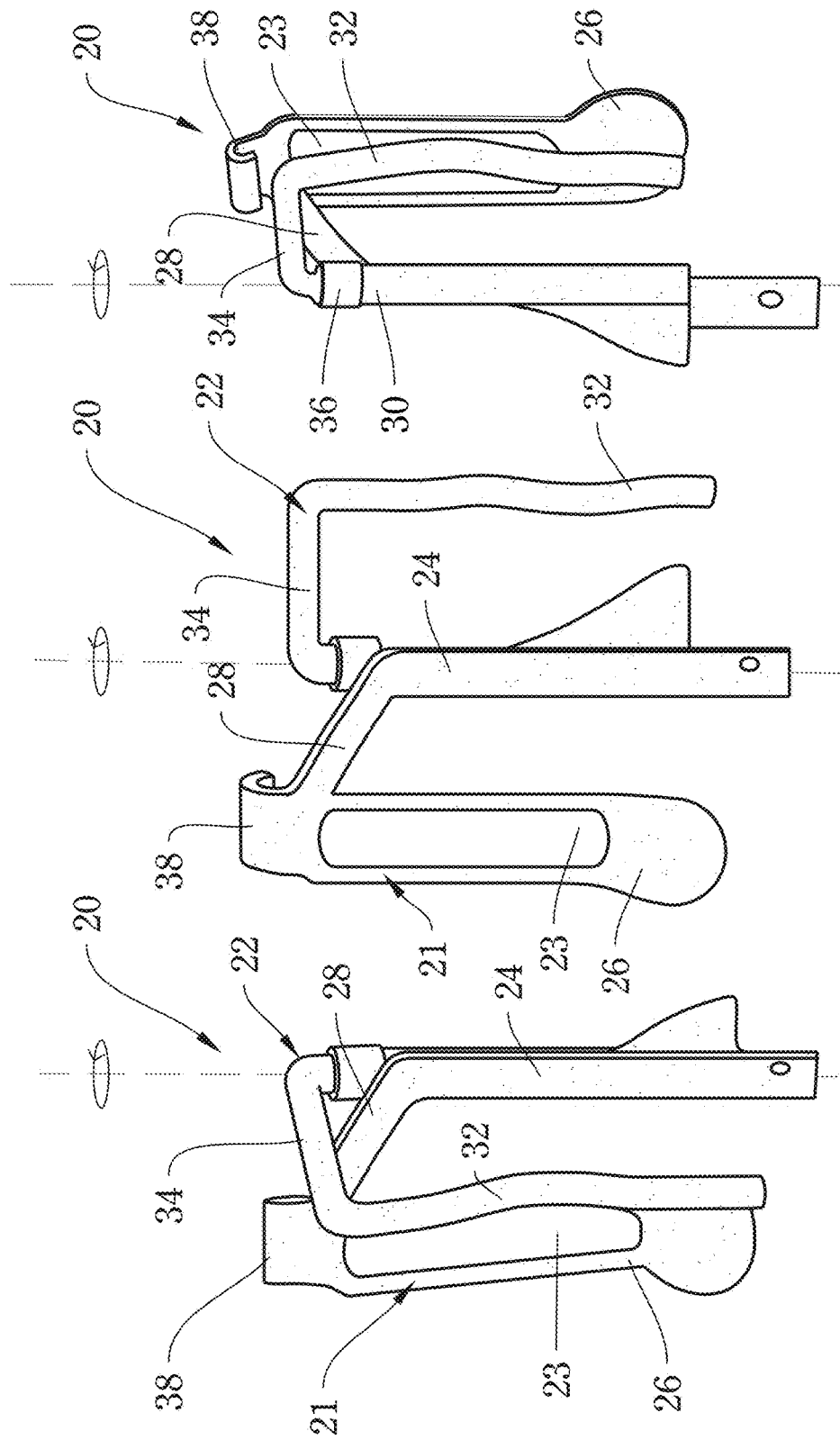

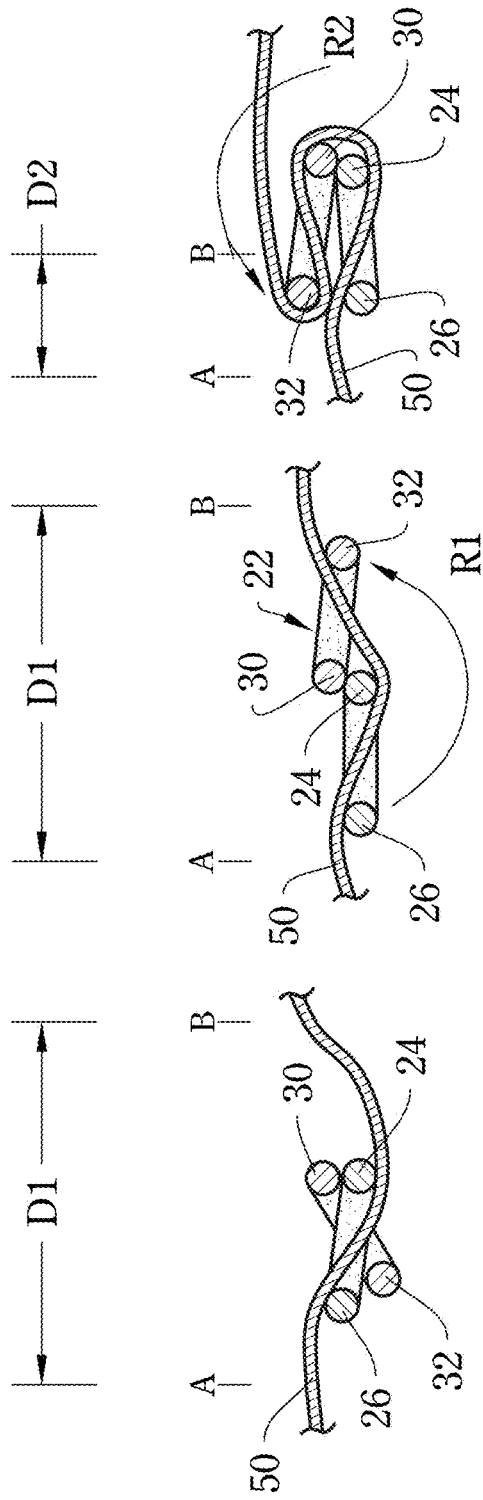

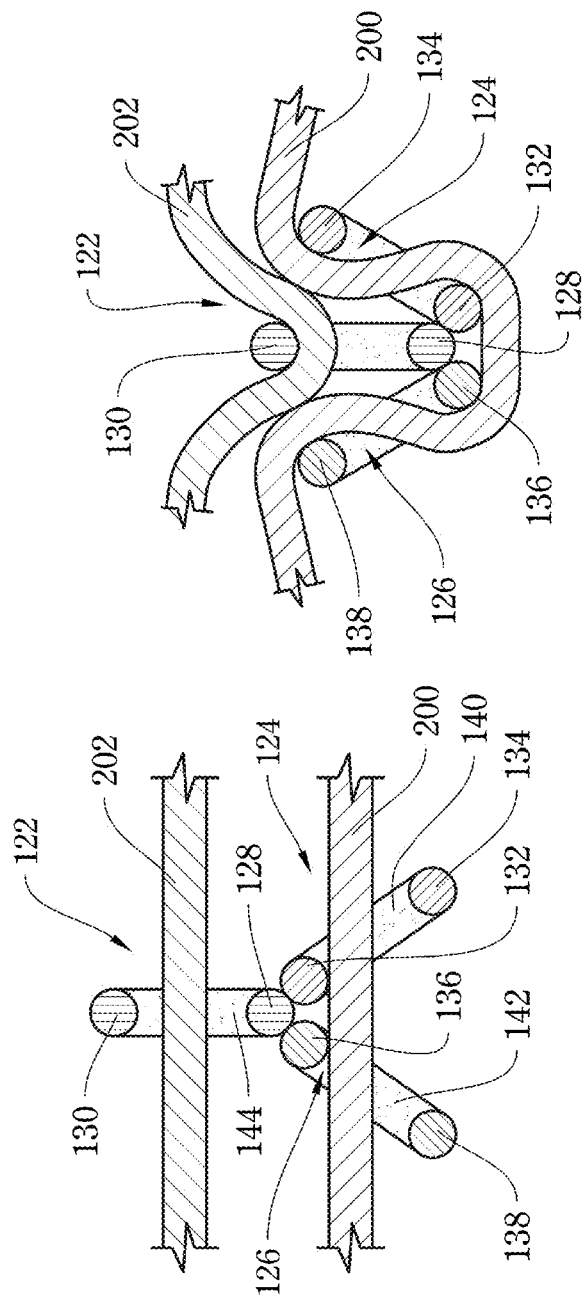

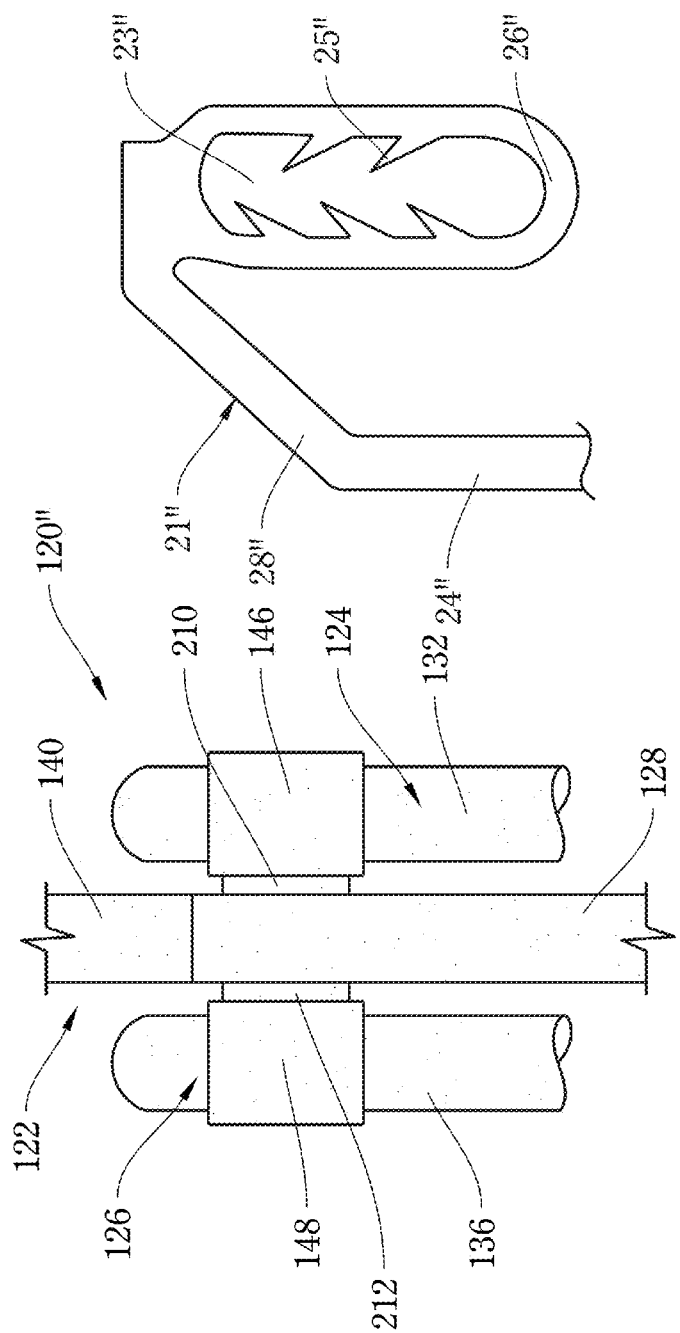

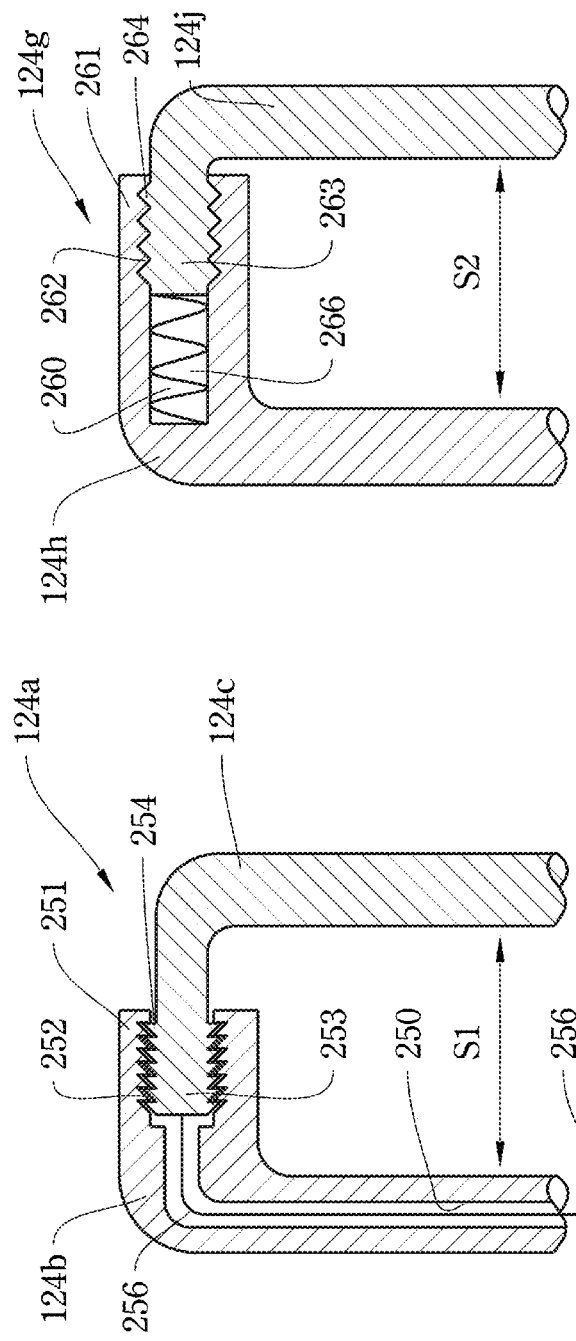

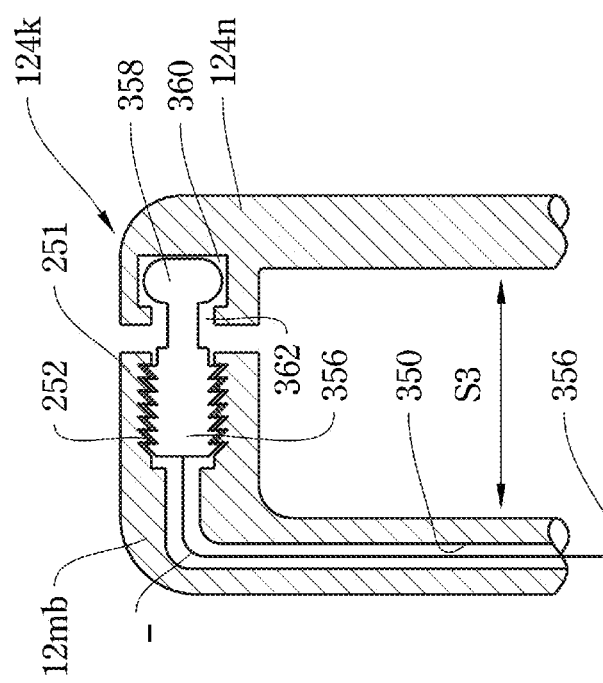

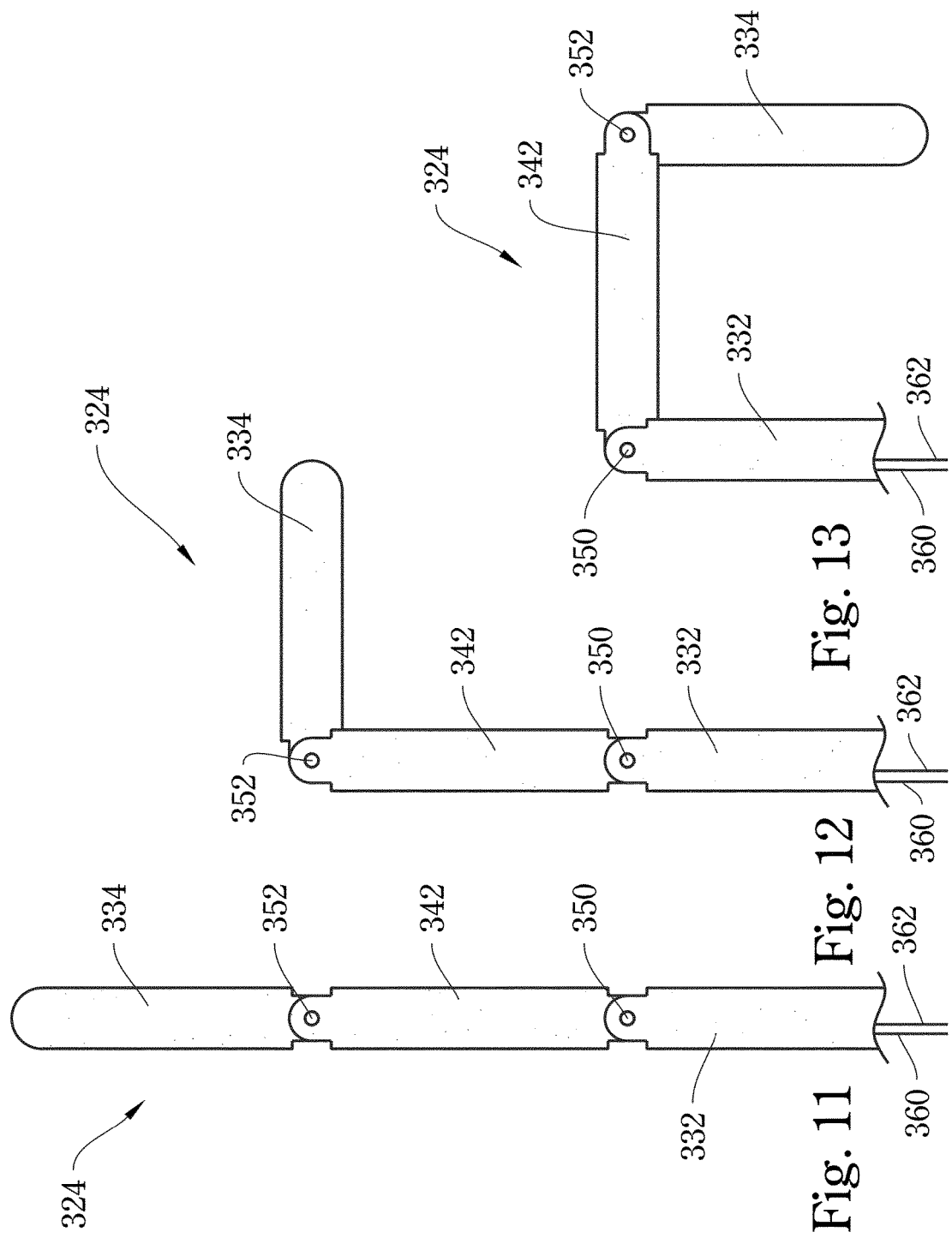

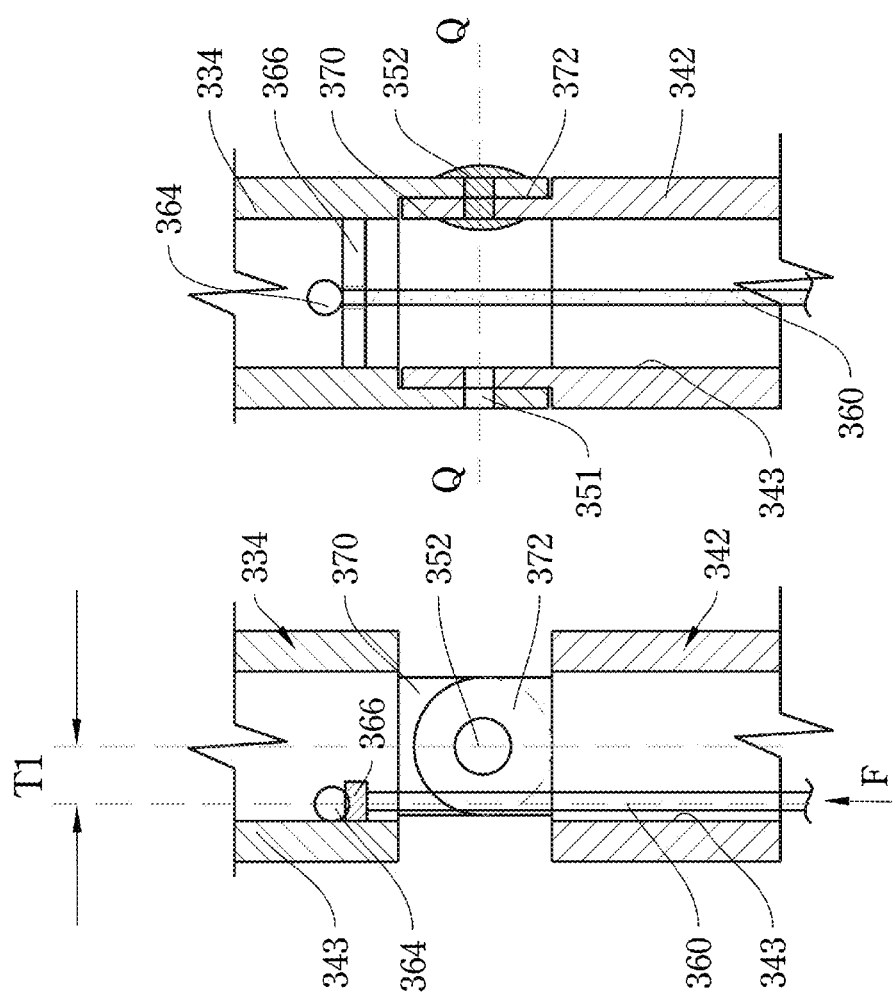

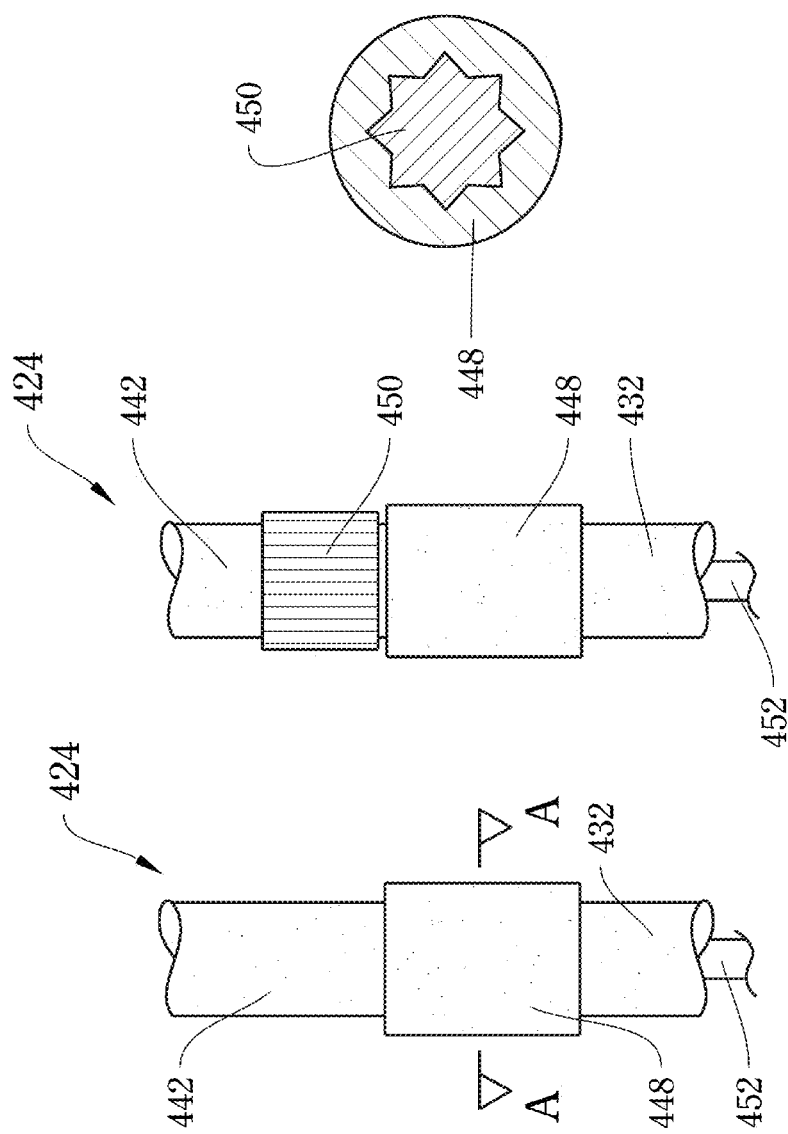

SYSTEM AND METHOD FOR PLICATING A HEART VALVE

BACKGROUND

The present invention relates generally to medical methods, devices, and systems. In particular, the present invention relates to methods, devices, and systems for the endovascular, percutaneous or minimally invasive surgical treatment of bodily tissues, such as tissue approximation or valve repair. More particularly, the present invention relates to repair of valves of the heart and venous valves.

Surgical repair of bodily tissues often involves tissue approximation and fastening of such tissues in the approximated arrangement. When repairing valves, tissue approximation includes coapting the leaflets of the valves in a therapeutic arrangement which may then be maintained by fastening or fixing the leaflets. Such coaptation can be used to treat regurgitation which most commonly occurs in the mitral valve.

Mitral valve regurgitation is characterized by retrograde flow from the left ventricle of a heart through an incompetent mitral valve into the left atrium. During a normal cycle of heart contraction (systole), the mitral valve acts as a check valve to prevent flow of oxygenated blood back into the left atrium. In this way, the oxygenated blood is pumped into the aorta through the aortic valve. Regurgitation of the valve can significantly decrease the pumping efficiency of the heart, placing the patient at risk of severe, progressive heart failure.

Mitral valve regurgitation can result from a number of different medical defects in the mitral valve or the left ventricular wall. The valve leaflets, the valve chordae which connect the leaflets to the papillary muscles, the papillary muscles or the left ventricular wall may be damaged or otherwise dysfunctional. Commonly, the valve annulus may be damaged, dilated, or weakened limiting the ability of the mitral valve to close adequately against the high pressures of the left ventricle.

The most common treatments for mitral valve regurgitation rely on valve replacement or repair including leaflet and annulus remodeling, the latter generally referred to as valve annuloplasty. A recent technique for mitral valve repair which relies on suturing adjacent segments of the opposed valve leaflets together is referred to as the "bow-tie" or "edge-to-edge" technique. While all these techniques can be very effective, they usually rely on open heart surgery where the patient's chest is opened, typically via a sternotomy, and the patient placed on cardiopulmonary bypass. The need to both open the chest and place the patient on bypass is traumatic and has associated high mortality and morbidity.

Consequently, alternative and additional methods, devices, and systems for performing the repair of mitral and other cardiac valves have been developed. Such methods, devices, and systems preferably do not require open chest access and are capable of being performed either endovascularly, i.e., using devices which are advanced to the heart from a point in the patient's vasculature remote from the heart, or by other minimally invasive approach.

One such technique involves plicating a valve leaflet so as to shorten a free edge of the leaflet. This shortening permits a better coaptation between opposing leaflets. One such technique is described in U.S. Publication 20160038149, where two U shaped hooks or clips, rotatable in relation to each other, are used to plicate a leaflet in a minimally invasive transcatheter technique.

The foregoing technique has been carried forward into a product known as the MitraClamp® by Heartworks LLC. FIGS. 1-3 show images of a device 20 that follows the MitraClamp concept. This device comprises two "U" shaped clips, a first clip 21, and a second clip 22 extending in the same direction. The first clip 21 comprises a first 24 and a second 26 downwardly descending prong which are connected to each other at an upper end by a first bridge 28. The second clip 22 comprises a third 30 and a fourth 32 downwardly descending prong, which are connected to each other at an upper end by a second bridge 34. At least one annular collar 36 is attached to the first prong 24 of the first clip 22. The third downwardly descending prong 30 passes through the collar 36 and is rotatable within the collar. This rotation allows the device 20 to assume a number of different conditions, some of which are exemplified in FIGS. 1, 2, and 3, as the second clip 22 rotates about an axis running up through the third prong 30 of the second clip 22.

The MitraClamp in operation may be envisaged with reference to FIGS. 1A, 2A, and 3A. These figures show how a free edge 50 of a leaflet of a valve in a patient's heart may be shortened in its free length by using the device 20. The figures show how the device may be positioned in relation to the free edge 50 of a leaflet in FIG. 1A, by inserting the device in the condition shown in FIG. 1 over a generally linearly extending free edge of a leaflet in a patient's heart, by known means. Once the device is introduced in this condition, the second clip 22 may be slowly rotated (by known means) around the axis of the third prong 30. In FIG. 2A, this rotation is indicated by the arrow R1 after the second clip 22 has been rotated 180 degrees. At this stage, the free edge 50 of the leaflet has not been plicated and is still in its starting condition shown in FIG. 1A. Then, the second clip is rotated a further 180 degrees as shown by arrow R2 in FIG. 3A. This final movement pulls the free edge 50 of the leaflet back towards the second prong 26 of the first clip 21, thereby folding (or plicating) the free edge of the leaflet 50 so that its net length is reduced. More specifically, two points A and B on the free edge of the leaflet are indicated in FIGS. 1A, 2A, and 3A. Before the plication, points A and B are a distance D1 apart from each other in the direction of the free edge 50 (FIG. 1A). After the plication, the points A and B are a much smaller distance D2 apart from each other in the direction of the free edge (FIG. 3A). When this condition has been achieved, the two clips are locked in relation to each other so that further movement is not possible. To achieve this locked result, an overhanging clasp 38 may be provided on bridge 28. The bridge 34 of the second clip 22 may be shaped to fit into the overhang of the clasp. The two clips are then fixed against linear movement in relation to each other (by known means). The delivery mechanism (not shown) may then be removed, and the clips 21, 22 are left behind in the heart of the patient, affixed to the free edge 50 of the leaflet which now has a reduced length. This result provides a better coaptation between the shortened leaflet and an opposing leaflet (not shown).

The device in the prior art as thus described still has many shortcomings. For, even when the leaflet has been plicated using this device, it may be found that the coaptation of the leaflets is not greatly improved because the device 20 itself prevents the two leaflets from forming an effective seal against each other during systole. Another problem is that the size of the device may be found to be inappropriate for the size of the leaflets when the device is positioned against the leaflets. At this stage of the procedure, it may be too late for the physician to withdraw the device and replace it with another differently sized device. Yet another problem is that the "U" shape of the clips in the device may render the device too large diametrically for easy delivery into the heart.

Therefore, devices, systems and methods are desired which may address the problems found in the art. At least some of these objectives will be met by the embodiments described herein below.

SUMMARY OF THE INVENTION

In one embodiment, the invention is a device for connecting together two opposing leaflets of a valve in a patient's heart. The device comprises a first clip having a generally U-shape comprising a first prong and a second prong, and a first bridge connecting the first prong to the second prong. The device further includes a second clip having a generally U-shape, comprising a third prong and a fourth prong, and a second bridge connecting the third prong to the fourth prong. The device further includes a third clip having a generally U-shape, comprising a fifth prong and a sixth prong, and a third bridge connecting the fifth prong to the sixth prong. Under this configuration, the third prong has a first elongate axis and the fifth prong has a second elongate axis and the third prong and the fifth prong are positioned to extend adjacent to and parallel with the first prong, and are configured to rotate about the first elongate axis and the second elongate axis respectively.

In some embodiments, a first collar is attached to the first prong and sized to rotatably receive the third prong, and a second collar is attached to the first prong and is sized to rotatably receive the fifth prong. Under this configuration, in some embodiments, the first collar may have a bore that has a non-circular internal shape, and the third prong has an external surface having a mating non-circular external shape, wherein the third prong is slideably advanceable through the first collar to disengage the non-circular external shape from the non-circular internal shape, and is retractable through the first collar to engage the non-circular external shape with the non-circular internal shape. In yet other embodiments, at least one of the first collar and the first prong are connected to each other through a first surface and a second surface, the first surface being formed from a polymer material having a glass point of not more than 50 degrees Celsius, and the second surface being formed from a ferromagnetic material. In some embodiments, the first surface comprises at least one of polyamide or polychlorotrifluoroethylene.

In some embodiments of the device, at least one of the first clip, the second clip, or the third clip comprises a proximal portion and a distal portion, the proximal portion defining an internal bore which is sized to movably receive a proximal end of the distal portion. Under this arrangement, the internal bore and an external surface of the proximal end of the distal portion may define mating teeth shaped to act as ratchet and pawl. In some embodiments, the internal bore and an external surface of the proximal end of the distal portion define mating helical threads shaped to provide relative axial movement upon relative rotation. In further embodiments, a spring may be positioned within the internal bore so as to bias the distal portion away from the proximal portion.

In some embodiments of the device each of the first clip, the second clip, and the third clip may comprise two pin joints configured to permit each of the first clip, the second clip, and the third clip to assume a straight condition for delivery, and a generally U-shape condition for implantation.

In further embodiments of the device the first clip may define an opening for receiving a portion of the second clip, the opening defining at least one barb shaped to engage with a leaflet that is forced into the opening.

In another embodiment, the invention is a method for connecting together a first leaflet to a second leaflet of a heart valve in a patient. The method comprises positioning a first clip having a generally U-shape such that the first leaflet passes through the generally U-shape of the first clip. Then, a second clip having a generally U-shape is positioned such that the second leaflet passes through the generally U-shape of the second clip, wherein the second clip is rotatably attached to the first clip by a first attachment surface. Then, a third clip having a generally U-shape is positioned such that the second leaflet passes through the generally U-shape of the third clip, wherein the third clip is rotatably attached to the first clip by a second attachment surface. Then, the second clip is rotated clockwise, thereby forcing the second leaflet into contact with the first leaflet at a first location. The third clip is then rotated counterclockwise thereby forcing the second leaflet into contact with the first leaflet at a second location.

In some embodiments, the method further includes locking the first clip, the second clip and the third clip into a fixed configuration. Under this arrangement, locking the first clip, the second clip and the third clip into a fixed configuration may include applying a first overhanging clasp between the first clip and the second clip, and applying a second overhanging clasp between the first clip and the third clip.

In other embodiments, the method may further include removing the first attachment surface and the second attachment surface from the device. In a preferred embodiment, removing the first attachment surface and the second attachment surface includes heating the first attachment surface and the second attachment surface, and heating the first attachment surface and the second attachment surface includes subjecting the first attachment surface and the second attachment surface to energy provided by a magnetic resonance source located outside the patient.

These and other advantages will become apparent when the invention is understood in conjunction with the drawings and the detailed description of some embodiments.

BRIEF DESCRIPTION OF THE DRAWINGS

FIG. 1 is a perspective view of a device known in the prior art for plicating a valve leaflet in a patient's heart, shown in a first condition.

FIG. 1A is a sectional view taken horizontally through the device of FIG. 1, additionally showing a leaflet weaving between the elements of the device in the first condition.

FIG. 2 is a perspective view of the device known in the prior art for plicating a valve leaflet in a patient's heart, shown in a second condition.

FIG. 2A is a sectional view taken horizontally through the device shown in FIG. 2, additionally showing a leaflet weaving between the elements of the device in the second condition.

FIG. 3 is a perspective view of a device known in the prior art for plicating a valve leaflet in a patient's heart, shown in a third condition.

FIG. 3A is a sectional view taken horizontally through the device of FIG. 3, additionally showing a leaflet weaving between the elements of the device in the third condition.

FIG. 5 is a sectional view of the device in FIG. 4, the section being taken horizontally at mid height through the device, showing a leaflet weaving between the elements of the device in the first condition.

FIG. 6 is a sectional view of the device in FIG. 4 in a second condition, showing the leaflet weaving between the elements of the device in the second condition.

FIG. 7 is an elevational view of a detail of the device in FIG. 4, showing features of a further embodiment of the invention.

FIG. 8 is an elevational view of a detail of another embodiment of the device in FIG. 4, showing features of a further embodiment of the invention.

FIG. 9 is a sectional view of a detail of another embodiment of the device in FIG. 4, showing features of a further embodiment of the invention.

FIG. 9A is another embodiment of the device shown in FIG. 9.

FIG. 10 is a sectional view of a detail of yet another embodiment of the device in FIG. 4, showing features of a further embodiment of the invention.

FIG. 11 is an elevational view of a component of yet a further embodiment of the invention shown in FIG. 4, showing features of the component in a first condition.

FIG. 12 is an elevational view of the component in FIG. 11, showing features of the component in a second condition.

FIG. 13 is an elevational view of the component in FIG. 11, showing features of the component in a third condition.

FIG. 14 is a front sectional view of a joint of the component in FIG. 11.

FIG. 15 is a side sectional view of the joint in FIG. 14.

FIG. 16 is an elevational view of a detail of an embodiment of the device shown in FIG. 4, shown in a first condition.

FIG. 17 is an elevational view of the detail in FIG. 16, shown in a second condition.

FIG. 18 is a sectional view taken substantially through the line A-A in FIG. 16.

DETAILED DESCRIPTION OF THE PREFERRED EMBODIMENTS

Figure 4:
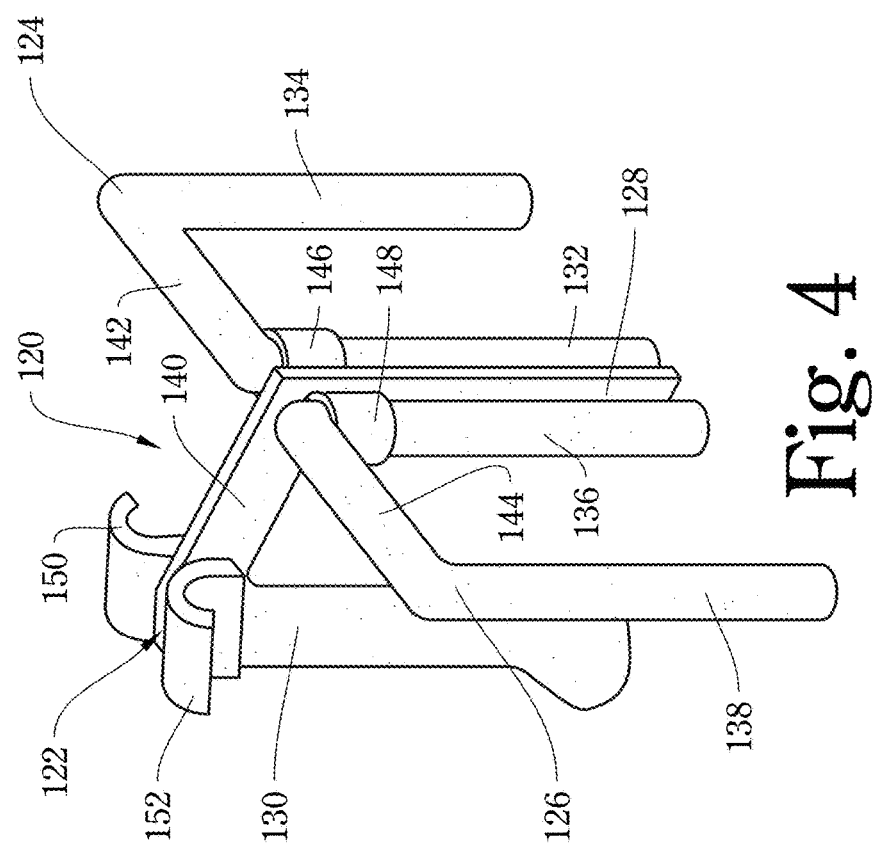
FIG. 4 is a perspective view of a device having features of one embodiment of the invention, shown in a first condition.

With reference to the figures a number of embodiments of the invention are described.

With reference to FIGS. 4-6, in a first embodiment the invention is a device 120 and a method for plicating a first leaflet of a heart valve, and simultaneously connecting the first leaflet to a second leaflet in order to reduce the overall amount of regurgitation in a valve. In an embodiment of the invention, the device comprises three "U" shaped clips, all oriented in the same direction which is shown to be downward in FIG. 4. A first clip 122, a second clip 124, and a third clip, 126 are arranged adjacent each other. Each clip has a first prong 128, 132, 136 respectively and a second prong 130, 134, 138 respectively. Each first prong and second prong are connected to each other by a bridge 140, 142, 144 respectively. The first prongs 128, 132, 136 are arranged to extend adjacent and parallel with each other as shown in FIG. 4. A first collar 146 and a second collar 148 are attached to the first prong 128 of the first clip 122. The first prong 132 of the second clip and the first prong 136 of the third clip extend through each collar respectively, so that the second clip and the third clip are free to rotate about axes extending along the first prong of each of these clips respectively. Attached to the bridge 140 of the first clip are two overhanging clasps 150, 152, each clasp being shaped to receive the bridges 140 and 142 of the second and third clips respectively, and to hold the bridges against movement for so long as the bridges are forced upwards into the clasps. The mechanism for locking the bridges in an upward condition are known in the art, and are not shown in FIG. 4.

In use, the device 120 is used as follows. The device is inserted on the end of a delivery catheter, using known transcatheter techniques, into the left atrium of a heart of a patient. Thus, in an inverted orientation from that shown in FIG. 4, the device may then lowered into and through the mitral valve. By manipulating the position of the device in relation to the two leaflets 200, 202 of the mitral valve, the operator may manipulate one of the leaflets (preferably the longer leaflet, the posterior leaflet) so that a free edge of the leaflet 200 extends inside the "U" of both the second clip 124 and the third clip 126 as shown in FIG. 5. Simultaneously, the free edge of the opposing shorter leaflet 202 is manipulated to extend through the "U" of only the first clip 122, as shown in FIG. 5. When the two opposing leaflets 200, 202 are thus arranged, the operator rotates the second clip 124 clockwise and the third clip 126 anticlockwise about their axes extending through the collars 146, 148. The two clips are rotated in opposite directions, so that the second prongs 134, 138 of each of these clips converge on the first prong 130 of the first clip, as shown in FIG. 6. This motion causes the first leaflet 200 to adopt a folded shape that pulls short the effective length of its free edge. Additionally, the motion causes a lesser shortening of the length of the free edge of the opposing leaflet 202. And furthermore, the motion effectively gives rise to a connection between the first leaflet 200 and the second leaflet 202 as shown in FIG. 6.

An advantage achieved by this device and its associated method is that the opposing leaflets 200, 202 are simultaneously shortened, and also are pinned to each other at a half way point or center point, producing a double bore valve from a single bore valve. Although the net size of the two openings in the valve are reduced compared to the original single opening, both effects are known to produce better coaptation between the leaflets, and thus to reduce the amount of regurgitation in the valve.

When the three clips of the device 120 are thus positioned in the folded condition, as shown in FIG. 6, the operator may lock the second and third bridges 140, 142 under the overhanging clasps 150, 152, and then may separate the device 120 from the delivery system (not shown) which is in turn removed from the heart in reverse transcatheter mode. The mitral valve is left with leaflets 200, 202 that are shortened in length, and clipped together at some point near their centers, thereby achieving an advantageous result for valve regurgitation. Other systems are known for clipping valve leaflets together at a center point, with beneficial effect. Such a system is the MitraClip® which is described in U.S. Pat. No. 8,052,592, the contents of which are incorporated herein by reference. However, the MitraClip does not have the advantageous ability to substantially shorten the leaflets by plication.

In another aspect of the invention described with reference to FIG. 7, the device may include features which will assist in situations where a clip device such as device 120 has been implanted in a valve in a patient's heart, but where the care-giver subsequently decides to insert a prosthetic heart valve into the valve opening in the heart by transcatheter means. As will be readily appreciated, if a clip type device has been implanted to connect opposing valve leaflets together, then it will ordinarily require removal of the device before a prosthetic valve can be inserted. This will be difficult where it is intended to implant the prosthetic device by transcatheter means, giving little access to the old clip device for removal.

The embodiment presently described seeks to address that problem, by giving the care-giver the option of disabling the device so as to undo the clipping action without cutting into the heart wall. This aspect will allow a prosthetic valve to be inserted into the bore of the valve, without the clip obstructing the insertion.

In one embodiment, a feature included in the device is shown with reference to FIG. 7, where portion of a device 120" is shown, having a first clip 122, a second clip 124, and a third clip 126. As in the previous embodiment, a first prong 128 of the first clip is flanked by a first prong 132 of the second clip and a first clip 136 of the third prong. A first collar 146 and a second collar 148 are attached to the first clip. However, in this embodiment, the attachment of the collars to the first clip is formed through a first connector 210 and a second connector 212, each connector attaching a collar onto the first prong respectively.

In one embodiment, the first clip 122, the collars 146, 148 may be formed from a ferromagnetic material such as iron or steel, which is selected for its tendency to heat up when exposed to a resonant magnetic field such as may be produced by a standard MRI (magnetic resonant imaging) machine. The first connector 210 and the second connector 212, however, may be formed from a polymer material with a suitable glass point Tg as described herein. Thus, if the polymer is selected to have a glass point of about 50 degrees Celsius, then, subjecting a patient with a clip device implanted to MRI of sufficient intensity will cause the collars to heat up to a point where the heat generated in the collars flows into the connectors, and the rigid structure of the connectors breaks down and allows the clip to decouple at the point of connection of the connectors 210, 212. A suitable polymer for this purpose is polyamide or polychlorotrifluoroethylene. It will be appreciated that, while the collars best serve the purpose when they are formed from a ferromagnitic material, it may be desirable that the prongs are not formed from ferromagnetic material because the heat they may generate would tend to injure the leaflets.

With reference to FIG. 6, it will be understood that decoupling the connectors 210, 212 will allow the first clip 122, the second clip 124, and the third clip 126 to break away from each other. This in itself may tend to create a problem that the clips may fall into the right septal chamber of the heart. However, a further aspect of the three clips in this embodiment is that they are provided during their manufacture with a suitable roughened surface, so that tissue growth from the leaflets is encouraged to embed the clips in the tissue of the leaflets during the time that the device is clipped onto the leaflets. Therefore, when the clips of the device are decoupled as described herein, they do not fall off the leaflets into the bottom of the septum of the heart, but remain attached to the leaflets, and allow the prosthetic device to be inserted into the open valve.

With reference to FIG. 8, another embodiment of the invention is shown wherein a feature is added to the known structure that is described in relation to FIGS. 1-3. In the known structure, the first clip 21 may define an opening 23 which allows the fourth downwardly descending prong 32 of the second clip 22 (which may be suitably bent) to nest inside the opening 23. Such nesting causes the leaflet to be folded in a more complex shape, and thus provides a better frictional hold on the leaflet via the phenomenon of bollard friction. In the present embodiment, the clip 21" includes downwardly descending prongs 24", 26" joined by a bridge 28", and in which an opening 23" is formed in the prong 26". Here however, the opening 23" further defines sharp barbs 25", that may be angled in a direction suitable for holding the leaflet more securely when it is forced into the opening 23" during the plication procedure.

With reference to FIG. 9, there is described yet another embodiment of a device of the kind described above, wherein the device includes a generally "U" shaped clip 124a. Features of this embodiment permit a surgeon who is implanting the clip in a heart valve of a patient to adjust the geometry of the clip 124a during the implantation procedure. The clip 124a comprises two portions, namely, a proximal portion 124b and a distal portion 124c, which together make up the "U" shape of the clip. Proximal portion 124b defines an internal bore 250. At a distal end 251, the bore may have a larger diameter than at the proximal end, and may define internal teeth 252 configured to provide a ratchet and pawl effect as will be described. Distal portion 124c defines, at a proximal end 253, external teeth 254. The proximal end 253 of distal portion 124c may be inserted into the bore 250 at the distal end 251 of proximal portion 124b, such that the internal teeth 252 and external teeth 254 interact with each other in a ratchet and pawl effect to control the advance of distal portion 124c into the bore of proximal portion 124b. In this embodiment, a force may be provided to cause the internal teeth 252 and external teeth 254 to move past each other. In one embodiment, the force may be applied prior to delivery, by the surgeon adjusting the length of the bridge of clip 124a. In another embodiment, this force may be provided after delivery, by actuation thread 256, which extends along the bore 250 and is firmly attached to the proximal end 253 of distal portion 124c. The presence of the actuation thread 256 permits the surgeon to adjust the spacing S1 between vertical elements of proximal portion 124b and distal portion 124c. As will be understood, with reference to FIGS. 5 and 6, an increased spacing S1 will provide greater shortening of the free edge of the leaflet that is being plicated. Thus, the surgeon can make small adjustments to the tension in the free edge of the leaflet during implantation of the device, either before implantation, or after implantation. After the device is set with the desired spacing S1, the activation thread 256 may be removed by giving it a sharp pull, thereby separating it from the device at the position of a frangible portion, as is known in the art.

With reference to FIG. 9A, there is described a variation on the above embodiment of a device of the kind described above, wherein the device includes a generally "U" shaped clip 124k. Features of this embodiment permit a surgeon who is implanting the clip in a heart valve of a patient to adjust the geometry of the clip 124k during the implantation procedure. The clip 124k comprises two portions, namely, a proximal portion 124m and a distal portion 124n, which together make up the "U" shape of the clip. Proximal portion 124m defines an internal bore 350. At a distal end 351, the bore may have a larger diameter than at the proximal end, and may define an internal threaded bore 352 configured to threadingly mate with a rotation element 356 situated inside the threaded bore 351. The rotation element is attached, at a proximal end thereof, to an activation element 356, which passes along the bore 350. The activation element 356 is configured to be rotatable within the bore 350 by the physician operator. At a distal end, the rotation element ends in a ball 358 which is sized to fit inside a chamber 360, but too large to pass through an opening 362 in the chamber. The described configuration allows the physician user to adjust the spacing S3 between vertical elements of proximal portion 124m and distal portion 124n with the same beneficial results as described above. A similar frangible structure is provided on the activation element 356 as on element 256 above to enable the physician to remove the activation element after use.

With reference to FIG. 10, in a variation on the previous embodiment, a "U" shaped clip 124g is provided that comprises proximal portion 124h and distal portion 124j. As in the previous embodiment, proximal portion 124h defines an internal bore 260 having internal teeth 262 at a distal end 261. The distal portion 124j defines external teeth 264 at a proximal end 263, wherein the teeth provide a ratchet and pawl effect to control movement of the portions in relation to each other. In this embodiment, the bore does not extend all the way to a proximal end, but terminates near the distal end 261. An internal spring 266 is provided in the bore, to bias the two portions apart. In this embodiment, the surgeon may elect to alter the spacing S2 manually, before commencing with the implantation process, based on an assessment of how much shortening of the valve leaflets will be needed. The surgeon simply manipulates the spacing S2 by hand, before commencing. The teeth of both portions lock the portions in a final configuration of suitable dimension.

In yet a further embodiment, a device such as the device 120 described above comprises three "U" shaped clips. One such clip 324 is exemplified in FIGS. 11-13. The other two clips may follow the same structural design as clip 324. In one aspect, the clip 324 is structured so that it may be unfolded from its "U" shape, to adopt a linear shape in a first condition for delivery, and may then be folded to adopt its "U" shape upon completion of delivery, for deployment.

Specifically, clip 324 is divided into three parts, namely a first prong 332, a second prong 334 and a bridge 342 which links the first prong to the second prong. Each of the prongs and the bridge define an internal bore 343 which extend continuously through the prongs and bridge. At points where the bridge 342 connects to the two prongs, the connection is formed to include a pin joint, specifically, by means of a pin 350 between the first prong 332 and the bridge 342, and a pin 352 between second prong 334 and bridge 342. With reference to FIGS. 14-15, it is shown that the structure of each of the prongs and the bridge at the location of connection is configured so that a prong 334 may rotate by up to 90 degrees in relation to the bridge 342. The prong 334 has a downwardly extending element 370 which overlaps with an upwardly extending element 372 on the bridge 342. An opening 351 is configured to extend through both the elements 370, 372 on the same axis Q-Q. A pin 352 is inserted into the opening to provide a pivoting joint between prong and bridge.

As further shown in FIGS. 14-15, a push element 360 is installed to extend through the bore 343. A proximal end of the push element extends all the way back to the proximal end of the delivery catheter (not shown) where it may be controlled by the surgeon. A distal end 364 of the push element extends beyond the pin 352, and is then attached to an internal wall of the bore 343. The attachment may be formed by solder, or mechanical attachment through a flange 366 or similar. Preferably, the push element 360 may be held against buckling at a plurality of points along its length, so that it may develop a high compression force or column strength. Preferably, the push element is attached to the internal wall of the bore 343 at a 90 degree offset from the axis Q-Q, so as to give the maximum possible lever arm "T1" as shown in FIG. 14. When the push element 360 is pushed under compression load with a force F (FIG. 14), then the prong 334 is placed under a rotational torque of F.T1, which causes it to bend as shown in FIG. 12. The same effect will occur when push element 362 is placed under compression load, bending the next joint so that the clip adopts the shape as shown in FIG. 13.

Another feature of each joint is that each of the prong and the bridge is fitted with mating detents, such that when the prong has been rotated by 90 degrees in relation to the bridge, the detents mate with each other in such a way that they snap into place and cannot be opened again. This allows the surgeon to give a sharp tug to the push elements 360, 362, thereby to detach their distal ends 364 from point of connection to the inner wall of the bore 343. Such detents are known in the art and are not exemplified in the figures.

With reference to FIGS. 16-18, in another embodiment, a device such as that described with reference to FIG. 4 is provided. In that device, downwardly extending clasps 150, 152 are provided on a first clip 122 in order to lock a second clip 124 and a third clip 126 in position. However, it may be found that, due to the thickness of the leaflets 200, 202 the second and third clips are not able to approach close enough to the first clip 122 to achieve the locking action with the clasps 150, 152. This problem may be understood with reference to FIG. 6, where it is shown that the second and third clips 124, 126 may not approach to within a close distance of the first clip 122. In such a case, the present embodiment may be used to overcome the problem. In this embodiment, the first prong (for example, the first prong 132 of the second clip 124) may be fitted with a feature such as described here with reference to FIGS. 16-18. In this embodiment, a collar 448 is provided that is attached to a first clip (not shown in FIGS. 16-18). The collar plays a similar function to the collars 146, 148 previously described with reference to FIG. 4. However, in this embodiment, the first prong 432 may be moved vertically through the collar, so that the first prong 432 and its associated bridge 442 may be moved both vertically, and rotated about the axis of the first prong. The first prong is connected to an actuation element 452 that extends downward to the proximal end of the catheter. The surgeon operating the device has control of the actuation element 452, and may extend it distally, then proximally, and may rotate it about its elongate axis. Furthermore, the internal bore of the collar 448 is shaped with gear shaped or other non-circular configuration as shown in FIGS. 17 and 18. A gear 450 attached to the first prong is shaped with mating gear shape, so that when proximal end gear 450 is inserted within the collar 448, the first prong and bridge cannot rotate in relation to the collar 448.

Thus, in use, the surgeon may locate the clip 424 into a location between opposing leaflets, as in FIG. 5. In order to rotate the clips into position as in FIG. 6, the surgeon pushes on the activation element 452 by an amount sufficient to extend the gear 450 out of the collar as in FIG. 17. This action advances the gear 450 out of the collar 448. At this point, the surgeon is free to rotate the actuation element 452, which causes the clip to rotate inside the collar 448. When the surgeon is satisfied that the amount of rotation is sufficient, she may pull the actuation element proximally, thereby inserting the proximal end of the bridge inside the collar, at which stage it is no longer free to rotate. The surgeon may pull the actuation element by a first activation force, which is sufficient to engage irreversible detents (not shown) located between the prong 432 and the actuation element inside the bore in the prong. The surgeon may then pull the actuation element by a second activation force, which is sufficient to rupture the actuation element at a frangible section, allowing the actuation element to break free and be removed from the patient, along with the delivery catheter.

Accordingly, there is described a novel system and method that addresses needs in the art. The present invention may, of course, be carried out in other specific ways than those herein set forth without departing from the essential characteristics of the invention. The present embodiments are, therefore, to be considered in all respects as illustrative and not restrictive, while the scope of the invention is set forth in the claims that follow.

We claim:

1. A device for connecting together two opposing leaflets of a valve in a patient's heart, comprising:
   a first clip having a generally U-shape, comprising a first prong and a second prong, and a first bridge connecting the first prong to the second prong;
   a second clip having a generally U-shape, comprising a third prong and a fourth prong, and a second bridge connecting the third prong to the fourth prong;
   a third clip having a generally U-shape, comprising a fifth prong and a sixth prong, and a third bridge connecting the fifth prong to the sixth prong;
   wherein the third prong has a first elongate axis and the fifth prong has a second elongate axis and the third prong and the fifth prong are positioned to extend adjacent to and parallel with the first prong, and are configured to rotate about the first elongate axis and the second elongate axis respectively.

2. The device of claim 1, wherein a first collar is attached to the first prong and sized to rotatably receive the third prong, and a second collar is attached to the first prong and is sized to rotatably receive the fifth prong.

3. The device of claim 2, wherein the first collar has a bore that has a non-circular internal shape, and the third prong has an external surface having a mating non-circular external shape, wherein the third prong is slideably advanceable through the first collar to disengage the non-circular external shape from the non-circular internal shape, and is retractable through the first collar to engage the non-circular external shape with the non-circular internal shape.

4. The device of claim 2, wherein at least one of the first collar and the first prong are connected to each other through a first surface and a second surface, the first surface being formed from a polymer material having a glass point of not more than 50 degrees Celsius, and the second surface being formed from a ferromagnetic material.

5. The device of claim 4, wherein the first surface comprises at least one of polyamide or polychlorotrifluoroethylene.

6. The device of claim 1, wherein at least one of the first clip, the second clip, or the third clip comprises a proximal portion and a distal portion, the proximal portion defining an internal bore which is sized to movably receive a proximal end of the distal portion.

7. The device of claim 6, wherein the internal bore and an external surface of the proximal end of the distal portion define mating teeth shaped to act as ratchet and pawl.

8. The device of claim 6, wherein the internal bore and an external surface of the proximal end of the distal portion define mating helical threads shaped to provide relative axial movement upon relative rotation.

9. The device of claim 6, wherein a spring is positioned within the internal bore so as to bias the distal portion away from the proximal portion.

10. The device of claim 1, wherein each of the first clip, the second clip, and the third clip comprises two pin joints configured to permit each of the first clip, the second clip, and the third clip to assume a straight condition for delivery, and a generally U-shape condition for implantation.

11. The device of claim 1, wherein the first clip defines an opening for receiving a portion of the second clip, the opening defining at least one barb shaped to engage with a leaflet that is forced into the opening.

12. A method for connecting together a first leaflet to a second leaflet of a heart valve in a patient, the method comprising:
   positioning a first clip having a generally U-shape such that the first leaflet passes through the generally U-shape of the first clip;
   positioning a second clip having a generally U-shape such that the second leaflet passes through the generally U-shape of the second clip, wherein the second clip is rotatably attached to the first clip by a first attachment surface;
   positioning a third clip having a generally U-shape such that the second leaflet passes through the generally U-shape of the third clip, wherein the third clip is rotatably attached to the first clip by a second attachment surface;
   rotating the second clip clockwise thereby forcing the second leaflet into contact with the first leaflet at a first location;
   rotating the third clip counter-clockwise thereby forcing the second leaflet into contact with the first leaflet at a second location.

13. The method of claim 12, further including locking the first clip, the second clip and the third clip into a fixed configuration.

14. The method of claim 13, wherein locking the first clip, the second clip and the third clip into a fixed configuration includes applying a first overhanging clasp between the first clip and the second clip, and applying a second overhanging clasp between the first clip and the third clip.

15. The method of claim 12, further including removing the first attachment surface and the second attachment surface.

16. The method of claim 15, wherein removing the first attachment surface and the second attachment surface includes heating the first attachment surface and the second attachment surface.

17. The method of claim 16, wherein heating the first attachment surface and the second attachment surface includes subjecting the first attachment surface and the second attachment surface to energy provided by a magnetic resonance source located outside the patient.

* * * * *